United States Patent [19]

Henrich

[11] 4,263,652
[45] Apr. 21, 1981

[54] OXYGEN SENSOR SIGNAL CONDITIONER

[75] Inventor: Robert S. Henrich, Farmington Hills, Mich.

[73] Assignee: The Bendix Corporation, Southfield, Mich.

[21] Appl. No.: 881,985

[22] Filed: Feb. 27, 1978

[51] Int. Cl.³ .................. F02B 75/10; F02D 28/00; G01N 31/00
[52] U.S. Cl. ................... 364/431; 73/1 G; 60/276; 123/440; 123/489; 364/482; 364/551
[58] Field of Search ............ 364/424, 431, 442; 123/32 EE; 60/276, 285; 73/1 G, 23

[56] References Cited

U.S. PATENT DOCUMENTS

| | | | |
|---|---|---|---|
| Re. 29,741 | 8/1978 | Norimatsu et al. | 364/431 |
| 3,745,768 | 7/1973 | Zechnall et al. | 60/276 |
| 3,938,075 | 2/1976 | Reddy | 60/285 |
| 3,948,228 | 4/1976 | Luchaco | 60/276 |
| 3,949,551 | 4/1976 | Eichler et al. | 60/285 |
| 3,969,614 | 7/1976 | Moyer et al. | 364/431 |
| 4,094,186 | 6/1978 | Wessel | 123/32 EE |
| 4,096,834 | 6/1978 | Norimatsu et al. | 123/32 EE |
| 4,099,495 | 7/1978 | Kiencke et al. | 123/32 EB |
| 4,103,649 | 8/1978 | Matumoto et al. | 123/32 EE |
| 4,106,450 | 8/1978 | Norimatsu et al. | 123/32 EE |
| 4,117,815 | 10/1978 | Ikeura | 123/32 EE |
| 4,121,554 | 10/1978 | Sueishi et al. | 123/32 EE |
| 4,130,095 | 12/1978 | Bowler et al. | 123/32 EE |
| 4,132,193 | 1/1979 | Takase et al. | 123/32 EE |
| 4,132,200 | 1/1979 | Asano et al. | 123/32 EE |
| 4,140,085 | 2/1979 | Rabus et al. | 123/32 EE |
| 4,153,023 | 5/1979 | Asano et al. | 60/285 |
| 4,167,163 | 11/1979 | Möder | 123/32 EE |

*Primary Examiner*—Felix D. Gruber
*Attorney, Agent, or Firm*—Gaylord P. Hass, Jr.; Russel C. Wells

[57] ABSTRACT

A method and apparatus for controlling the various functions of an internal combustion engine using a program-controlled microprocessor having a memory preprogrammed with various control laws and associated control schedules receives information concerning one or more engine-operating parameters such as manifold absolute pressure, throttle position, engine coolant temperature, air temperature, engine speed or period and the like. These parameters are sensed and then supplied to input circuits for signal conditioning and conversion into digital words usable by the microprocessor. The microprocessor system computes a digital command word indicative of a computer-commanded engine control operation and output circuitry responds to predetermined computer-generated commands and to the computed digital command words for converting them to corresponding pulse-width control signals for controlling such engine operations as fuel-injection ignition timing, proportional and/or on-off EGR control, or the like. The engine control system further includes an oxygen sensor feedback system for supplying signals indicative of the quantity of oxygen in the exhaust system of the engine back to the microprocessor for control purposes.

In particular this disclosure relates to an oxygen sensor condition circuit which generates not only the bilevel output signals indicating the quality of oxygen in the exhaust system, but also generates an oxygen sensor inhibit signal which may be used in a control system to effectively disregard the output of the sensor and to apply fixed or preprogrammed conditions for controlling the air/fuel ratio. Typically the purpose of the inhibit signal is to indicate when the sensor is inoperable because of its operating temperature or its physical condition.

8 Claims, 2 Drawing Figures

Oxygen Sensor Signal Conditioning System

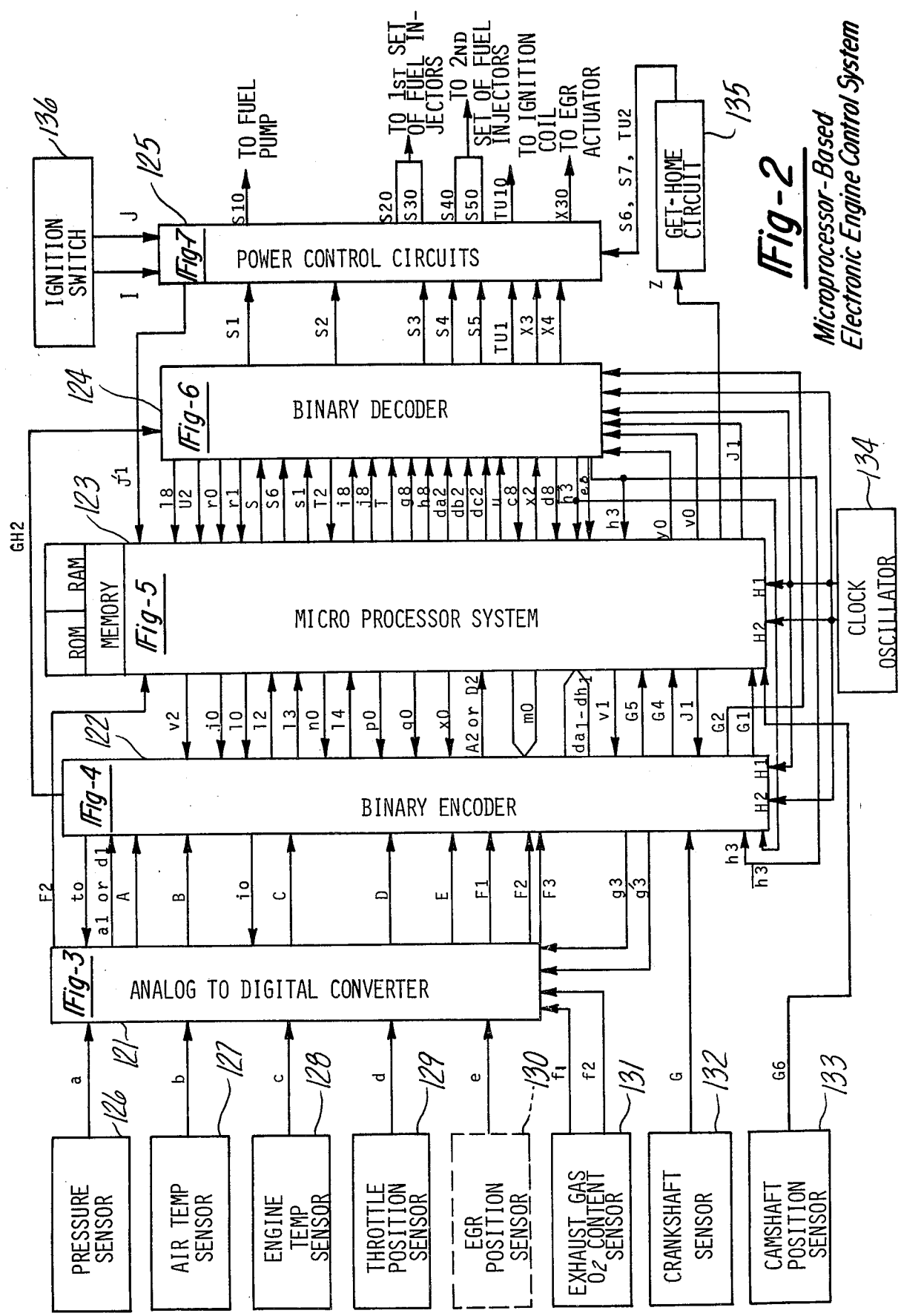

Oxygen Sensor Signal Conditioning System

OXYGEN SENSOR SIGNAL CONDITIONER

BACKGROUND OF THE INVENTION

1. Field of the Invention

This invention relates generally to a method and apparatus for controlling an internal combustion engine, and more particularly to a microprocessor-based electronic engine control system having a memory preprogrammed with various control laws and control schedules responsive to one or more sensed engine-operating parameters for generating signals for controlling fuel injection, ignition timing, EGR control, or the like.

2. Statement of the Prior Art

Many of the patents of the prior art recognize the need for employing the enhanced accuracy of digital control systems for more accurately controlling one or more functions of an internal combustion engine.

U.S. Pat. No. 3,969,614 which issued to David F. Moyer, et al on July 13, 1976 is typical of such systems as are U.S. Pat. No. 3,835,819 which issued to Robert L. Anderson, Jr. on Sept. 17, 1974; U.S. Pat. No. 3,904,856 which issued to Louis Monptit On Sept. 9, 1975; and U.S. Pat. No. 3,906,207 which issued to Jean-Pierre Rivere, et al on Sept. 16, 1975. All of these Patents represent a break-away from the purely analog control systems of the past, but neither the accuracy, reliability, or number of functions controlled is sufficient to meet present day requirements.

Future internal combustion engines will require that emissions be tightly controlled due to ever-increasing governmental regulations, while fuel consumption is minimized and drivability improved over the entire operating range of the engine. None of the systems of the prior art provide a method and apparatus for controlling the operation of an internal combustion engine over even a portion of its operating range with sufficient accuracy to attain minimal emissions and minimal fuel consumption along with improved drivability.

Many of the systems of the prior art have attempted to utilize feedback from oxygen sensors located in the exhaust system for controlling various engine-operating conditions. These attempts were met with little success due to the relative unreliability of the present day oxygen sensors and the inability of such sensors to produce signals of significant magnitude on either side of stiochiometric air-fuel ratios.

The application of the present invention permits the use of an oxygen sensor feedback system for control purposes by ensuring that the oxygen sensor signals are properly conditioned and for testing sensor temperature and generating an inhibit signal to inform the computing system that a low temperature condition exist and hence that the possibility of unreliable sensor readings exists.

SUMMARY OF THE INVENTION

The system of the present invention contemplates an oxygen sensor being placed in the exhaust gas stream of an internal combustion engine for sensing the level of uncombined oxygen existing therein. The oxygen sensors impedance is monitored to derive an oxygen sensor inhibit signal when the voltage developed across the sensor exceeds a fixed level for a specified current applied to the sensor. In the preferred embodiment of the present invention, a two-sensor installation was used whereby a first oxygen sensor was placed in one bank of an exhaust manifold while a second oxygen sensor was placed in the other bank. A monitoring amplifier is associated with each channel and a comparator is operatively coupled to the output of each amplifier. A predetermined threshold indicative of stiochiometric operation is established at one input of the comparator and the amplified sensor output is applied to the other. The signal conditioner of the present invention also controls the current to the sensors for impedence monitoring and greatly enhances the feedback system's ability to distinguish the difference between "rich" and "lean" signals from those caused by sensor high impedance due to low temperatures, etc. Furthermore, the present invention provides means for optimizing the current supplied to the sensor, the inhibit threshold level, and a stiochiometric threshold level so as to produce properly conditioned signals capable of being used by said microprocessor-based engine control system for computing highly precise engine control commands.

INCORPORATION BY REFERENCE

This application is one of fourteen application filed on Feb. 27, 1978, all commonly assigned and having substantially the same specification and drawings, the fourteen applications being indentified below:

| Serial Number | Title |
| --- | --- |
| 881,321 | Microprocessor-Based Electronic Engine Control System |
| 881,322 | Feedback-Compensated Ramp-Type Analog to Digital Converter |
| 881,323 | Input/Output Electronic For Microprocessor-Based Engine Control System |
| 881,324 | Swtiching Control of Solenoid Current in Fuel Injection Systems |
| 881,921 | Dual Voltage Regulator With Low Voltage Shutdown |
| 881,922 | Oxygen Sensor Qualifier |
| 881,923 | Ratiometric Self-Correcting Single Ramp Analog To Pulse Width Modulator |
| 881,924 | Microprocessor-Based Engine Control System Acceleration Enrichment Control |
| 881,925 | Improvements in Microprocessor-Based Engine Control Systems |
| 881,981 | Oxygen Sensor Feedback Loop Digital Electronic Signal Integrator for Internal Combustion Engine Control |
| 881,982 | Improvements in Electronic Engine Controls System |
| 881,983 | Electronic Fuel Injection Compensation |
| 881,984 | Ignition Limp Home Circuit For Electronic Engine Control Systems |
| 881,985 | Oxygen Sensor Signal Conditioner |

Application Ser. No. 881,321, filed Feb. 27, 1978 now U.S. Pat. No. 4,255,789 that application is specifically incorporated herein by reference.

For a better understanding of the drawing figures in this application, reference is made to the same figure numbers in the above mentioned application Ser. No. 881,321, which includes FIGS. 1 to 34.

BRIEF DESCRIPTION OF THE DRAWINGS

FIG. 2 is a block diagram of the microprocessor-based electronic engine control system.

Figure 3E:
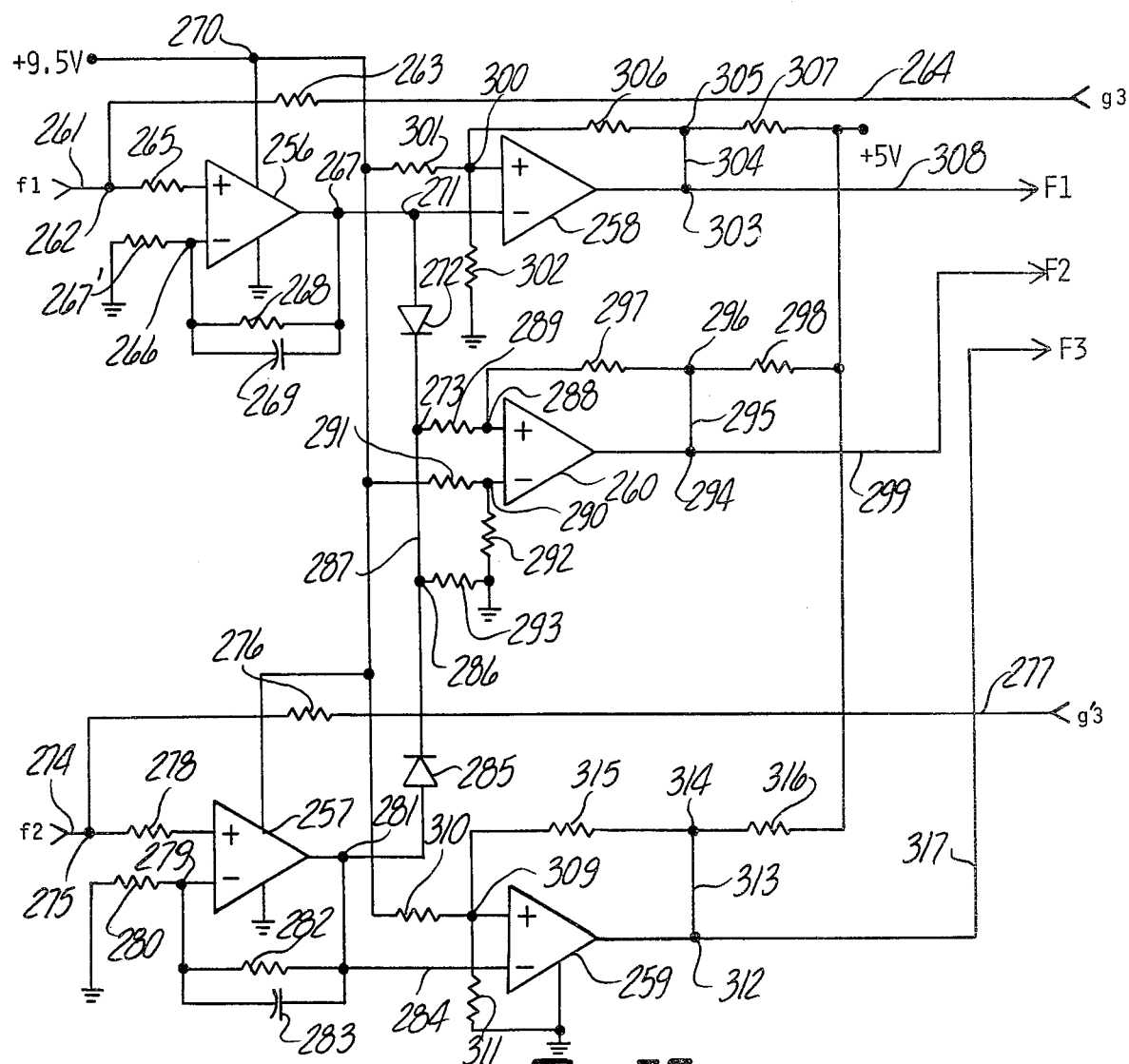
FIG. 3E is an electrical schematic diagram of the preferred embodiment of the oxygen sensor signal conditioning system.

I claim:

1. In a system employing at least one conventional zirconia-type oxygen sensor for measuring the relative level of uncombined oxygen in a given gas mixture and generating an oxygen sensor output signal having a first general voltage level if less than a predetermined percentage of uncombined oxygen is present in said gas mixture and a second general voltage level if at least said predetermined percentage of uncombined oxygen is present in said gas mixture, said zirconia-type oxygen sensor being characterized in that its impedance decreases as its operating temperature increases and in that measurements taken below some predetermined minimum temperature such as 300° Centigrade are inherently unreliable due to excessively high sensor impedance, an oxygen sensor output signal conditioning system for insuring that only reliable, properly conditioned electrical signals indicative of the measured relative level of uncombined oxygen in said given gas mixture are outputted for measurement or control purposes, said oxygen sensor output signal conditioning system comprising:

means for supplying a test current to said oxygen sensor and generating an oxygen sensor test output signal indicative of the impedance of said oxygen sensor, said sensor impedance being a function of sensor temperature;

monitoring amplifier means having relatively little current flowing into or out of its input terminals for amplifying said oxygen sensor output signal and said oxygen sensor test output signal;

comparator means having first and second comparator inputs and a comparator output, said first comparator input being operatively coupled to the output of said monitoring amplifier means for receiving the amplified output of said oxygen sensor output signal therefrom;

means operatively coupled to said second comparator input for establishing a predetermined reference threshhold voltage level indicative of a stoichiometric mixture of uncombined oxygen in said given gas mixture, said comparator output normally generating a first comparator output state indicating that the measured level of uncombined oxygen is "lean" of stoichiometric so long as the amplified value of said oxygen sensor output signal is at said first general voltage level and therefore less than the value of said established predetermined threshold voltage level, said comparator output being responsive to the amplified value of said oxygen sensor output signal being at said second general voltage level and therefore being greater than said established predetermined threshold voltage level for rapidly switching to a second comparator output state indicating that the measured level of uncombined oxygen in said given gas mixture is "rich" of stoichiometric;

test comparator means having first and second comparator inputs and a test comparator output, said first test comparator input being operatively coupled to the output of said monitoring amplifier means for receiving said amplified oxygen sensor test output signal therefrom;

means operatively coupled to said second test comparator input for establishing a predetermined test threshold voltage level indicative of a predetermined maximum sensor impedance value and therefore a minimum sensor operating temperature, the output of said test comparator means normally generating a non-inhibit test comparator output signal so long as the value of said amplified oxygen sensor test output signal is less than said established test threshold voltage level, said output of said test comparator means being responsive to the value of said amplified oxygen sensor test output signal being greater than said established test threshold voltage level for rapidly switching to generate an INHIBIT test comparator output signal, the state of the output signal of said test comparator means indicating whether said properly amplified and conditioned comparator output state signals indicative of the relative measured level of uncombined oxygen in said given gas mixture are sufficiently reliable to be used for measurement and control purposes.

2. The oxygen sensor output signal conditioning system of claim 1 wherein said means for supplying a test current to said oxygen sensor includes a relatively large valued resistive means for selectively regulating said test current, said resistive means being operatively coupled between a source of test potential and an input of said monitoring amplifier for supplying said test current to said oxygen sensor and logic means for periodically enabling said test current to be applied to said oxygen sensor on a sampling basis, said logic means further including means for temporarily storing the test comparator output signal resulting from the last sensor testing for indicating whether said comparator output state signals indicative of the relative measured level of uncombined oxygen in said given gas mixture are reliable or unreliable.

3. The oxygen sensor output signal conditioning system of claim 1 wherein said monitoring amplifier means includes a non-inverting operational amplifier having MOS FET inputs for allowing only a very small current to flow into and out of said amplifier inputs, said operational amplifier having first and second amplifier inputs and an amplifier output, said first amplifier input being resistively coupled to an input node for isolation purposes, said input node being opertively coupled for receiving said test current and to the output of said oxygen sensor for receiving said oxygen sensor output signals therefrom, and means for coupling said second amplifier input to ground and to said amplifier output for gain control and feedback purposes.

4. In an internal combustion engine having an intake system, an exhaust system, an engine block, a plurality of cylinders disposed in said engine block, a piston operatively mounted for reciprocal movement within each of said plurality of cylinders in response to the combustion of fuel and air therein, means disposed at least partially within said intake system for controlling the quantity of air supplied to said cylinders, means for supplying a controlled quantity of fuel to one or more of said plurality of cylinders, control means responsive to one or more predetermined control signals for operatively varying the ari-fuel mixture in said engine, first and second oxygen sensors, one oxygen sensor being operatively disposed in each of the two major exhaust streams of said internal combustion engine, each of said oxygen sensors being responsive to the relative air-fuel mixture existing in said corresponding exhaust stream and generating an oxygen sensor output signal having a first general voltage level if said measured air-fuel ratio is "lean" of stoichiometric and a second general voltage level if said measured air-fuel ratio is "rich" of stoichiometric, each of said oxygen sensors being characterized in that the impedance thereof decreases as its operating temperature increases and in that measurements taken below some minimum temperature such as 300° Centigrade are inherently unreliable due to excessively high internal sensor impedance, an oxygen sensor output signal conditioning system for insuring that only reliable output signals indicative of said rich or lean air-fuel mixture measurements are outputted for control purposes, said oxygen sensor output signal conditioning system comprising:

first and second means for supplying first and second test currents to said first and second oxygen sensors, respectively, and producing corresponding first and second oxygen sensor test output signals indicative of the measured sensor impedance, which is a function of sensor-operating temperatures, said first and second test current supply means being utilized to avoid cross-coupling of test currents and sensor signals between said first and second oxygen sensors;

first and second monitoring amplifiers having relatively little current flowing into or out of their input terminals for amplifying said first and second oxygen sensor output signals and said first and second oxygen sensor test output signals from said first and second oxygen sensors, respectively, and for optimizing the test current supplied to said first and second sensors by said first and second test current supply means via the high input impedance of said first and second monitoring amplifiers;

first and second output comparators each having first and second comparator inputs and a comparator output, the first input of each of said first and second output comparators being operatively coupled to receive said oxygen sensor output signals and said oxygen sensor test output signals from said first and second oxygen sensors, respectively;

first and second means operatively coupled to the second comparator inputs of said first and second output comparators for establishing a reference threshold voltage level indicative of a stoichiometric air-fuel ratio, the output of each of said first and second output comparators normally having a first value when said measured air-fuel ratio is lean of stoichiometric so long as the amplified value of said corresponding oxygen sensor output signal is at said first general voltage level and therefore less than said established predetermined threshhold voltage level, the comparator output of each of said first and secon output comparators being responsive to the amplified value of said corresponding oxygen sensor output signal being at least equal to said second general voltage level and therefore being greater than said established predetermined threshhold voltage level for rapidly switching to a second value indicating that the measured air-fuel ratio is rich of stoichiometric;

a single test comparator having first and second test comparator inputs and a test comparator output;

first and second diode means operatively coupling the output of said first and second monitoring amplifier to said first test comparator input for receiving either of said amplified first and second oxygen sensor test output signals from said corresponding first and second monitoring amplifier means;

means operatively coupled to said second test comparator input for establishing a test threshhold level indicative of a predetermined maximum sensor impedance value and therefore a minimum sensor temperature, the output of said test comparator normally generating a GO signal so long as the value of said amplified oxygen sensor test output signals from both of said first and second monitoring amplifiers are less than said established test threshhold voltage level, said test comparator output being responsive to the value of said amplified oxygen sensor test output signals from either of said first and second monitoring amplifiers being greater than said established test threshhold voltage level for rapidly switching to generate an INHIBIT signal, the signal at the output of said test comparator indicating whether said first and second comparator output state signals indicative of a measured lean or rich air-fuel ratio in said exhaust system are sufficiently reliable to be used for generating one or more of said predetermined control signals.

5. The system of claim 4 wherein each of said first and second means for supplying a test current includes a relatively large valued resistive means for selectively regulating said test current, said resistive means being operatively coupled between a source of test potential and the input of said monitoring amplifier for supplying said test current to said oxygen sensor, and logic means for periodically enabling said test current to be applied to said oxygen sensor on a sampling basis, said logic means further including means for temporarily storing the GO or INHIBIT output state signal of said test comparator resulting from the last sensor testing for indicating whether said first and second values indicative of the relative measured level of uncombined oxygen in said given gas mixture are reliable or unreliable.

6. The system of claim 4 wherein each of said first and second monitoring amplifiers includes a non-inverting operational amplifier having MOS FET inputs for allowing only a very small current to flow into and out of said amplifier inputs, said operational amplifier having first and second amplifier inputs and an amplifier output, said first amplifier input being resistively coupled to an input node for isolation purposes, said input node being operatively coupled for receiving said test current and to the output of said oxygen sensor for receiving said oxygen sensor output signals therefrom, and means for coupling said second amplifier input to ground and to said amplifer output for gain control and feedback purposes.

7. An oxygen sensor signal conditioner system wherein the oxygen sensor generates a signal voltage, said system comprising:

means for comparing the oxygen sensor signal voltage level with a first threshold voltage level indicative of a stoichiometric air-fuel ratio for generating a first signal indicative of one of either a rich or a lean air-fuel ratio whenever the sensor signal voltage is less than said first threshold level and for generating a second signal indicative of the other one of said rich or lean air-fuel ratio whenever the sensor signal voltage is greater than said first threshold level;

pulsed current source means for periodically testing the impedance of an oxygen sensor and operable to generate a pulsed voltage signal in response thereto which pulsed voltage signal is proportional to the impedance of the oxygen sensor;

means for generating a second threshold voltage level which level is higher than either said first or second signal voltages; and means for comparing said pulsed voltage signal and said second threshold voltage level for generating an oxygen sensor inhibit signal whenever said pulsed voltage signal is greater than said second threshold voltage level.

8. In an internal combustion engine system wherein at least one oxygen sensor is operatively disposed in the exhaust system for supplying feedback information for controlling the air-fuel ratio of the system, an improved method of accurately distinguishing between oxygen sensor output signals indicative of a rich air-fuel mixture, a lean air-fuel mixture, and those due to high internal oxygen sensor impedance which often occur when said oxygen sensor is relatively cold, said method comprising the steps of:

monitoring the relative percentage of uncombined oxygen existing in the exhaust system as a measure of the actual air-fuel ratios of said internal combustion engine system;

generating a first oxygen sensor output signal when a "lean" air-fuel condition is detected and a second oxygen sensor output signal when a "rich" air-fuel ratio is detected;

periodically generating a test current and transmitting said test current to said oxygen sensor for measuring the internal impedance thereof as an indication of the reliability of said oxygen sensor output signals;

generating an oxygen sensor test output signal in response to the receipt of said test current, said oxygen sensor test output signal being indicative of the measured internal impedance of said oxygen sensor;

amplifying said oxygen sensor output signal and said oxygen sensor test output signal;

comparing said oxygen sensor output signals to a predetermined reference voltage level representing a stoichiometric air-fuel ratio and generating a first comparator output when said first oxygen sensor output signal proves to be less than said predetermined reference voltage to indicate a measured air-fuel ratio which is lean of stoichiometric and for generating a second comparator output signal when said second oxygen sensor output signal proves to be greater than said predetermined reference voltage indicating a measured air-fuel ratio which is rich of stoichiometric;

comparing said oxygen sensor test output signal with a predetermined inhibit threshhold voltage level representing that oxygen sensor impedance and hence that oxygen sensor operating temperature below which said comparator outputs indicative of rich or lean measured air-fuel ratios are to be assumed unreliable and for generating an INHIBIT signal whenever said oxygen sensor test output signal is greater than said predetermined inhibit threshhold voltage level indicating that the inherent impedance of said oxygen sensor is too great to permit a reliable measurement of the air-fuel ratio existing in said exhaust system and for generating a GO signal whenever said oxygen sensor test output signal is less than said predetermined inhibit threshhold voltage level indicating that all first and second oxygen sensor output signals are reliable and may be used for generating control signals for selectively increasing and decreasing the air-fuel ratio in said engine system.

* * * * *